US006572788B2

(12) United States Patent
Walker

(10) Patent No.: US 6,572,788 B2
(45) Date of Patent: Jun. 3, 2003

(54) AMINE OXIDE WOOD PRESERVATIVES

(75) Inventor: Leigh E. Walker, Macungie, PA (US)

(73) Assignee: Lonza, Inc., Fair Lawn, NJ (US)

( * ) Notice: Subject to any disclaimer, the term of this patent is extended or adjusted under 35 U.S.C. 154(b) by 0 days.

(21) Appl. No.: 09/864,887

(22) Filed: May 24, 2001

(65) Prior Publication Data
US 2002/0026883 A1 Mar. 7, 2002

Related U.S. Application Data

(60) Provisional application No. 60/285,863, filed on Apr. 23, 2001, and provisional application No. 60/206,751, filed on May 24, 2000.

(51) Int. Cl.$^7$ .............................. C09K 3/00; C11D 1/75; C23F 11/12; C23F 11/14; C09D 5/14; A61K 47/00
(52) U.S. Cl. ................... 252/380; 252/602; 252/401; 252/390; 510/199; 510/433; 106/18.32; 424/126; 422/16
(58) Field of Search ................... 252/401, 390, 252/602, 380; 510/199, 383, 433; 106/18.32, 18.33; 427/429, 430.1, 303, 325; 424/126; 422/16

(56) References Cited

U.S. PATENT DOCUMENTS

| 3,296,145 A | 1/1967 | Findlan et al. ............... 252/106 |
|---|---|---|
| 3,484,523 A | 12/1969 | Findlan et al. ............... 424/248 |
| 3,761,488 A | 9/1973 | Lewis et al. ................. 260/302 |
| 4,005,193 A | 1/1977 | Green et al. ................. 424/168 |
| 4,105,431 A | 8/1978 | Lewis et al. .................... 71/67 |
| 4,379,810 A | 4/1983 | Amundsen et al. .......... 428/541 |
| 4,382,105 A | 5/1983 | Amundsen et al. .......... 427/370 |
| 4,622,248 A | 11/1986 | Leach et al. ................. 427/440 |
| 4,857,322 A | 8/1989 | Goettsche et al. ........... 424/633 |
| 4,929,454 A | 5/1990 | Findlay et al. ............... 424/638 |
| 4,937,143 A | 6/1990 | West ........................ 427/419.8 |
| 4,950,685 A | 8/1990 | Ward ........................... 514/479 |
| 5,073,570 A | 12/1991 | Tseng .......................... 514/533 |
| 5,276,029 A | 1/1994 | Goettsche et al. ........ 514/231.2 |
| 5,304,237 A | 4/1994 | Barth et al. ................. 106/18.3 |
| 5,426,121 A | 6/1995 | Bell ............................. 514/500 |
| 5,468,284 A | 11/1995 | Sturm ............................ 106/2 |
| 5,486,315 A | 1/1996 | Tseng |
| 5,527,384 A | 6/1996 | Williams et al. .......... 106/18.32 |
| 5,536,505 A | 7/1996 | Wilson et al. ............ 106/18.33 |
| 5,833,741 A | 11/1998 | Walker ........................... 106/2 |
| 5,922,672 A | 7/1999 | Stringer et al. |
| 6,063,290 A | 5/2000 | Failon et al. |
| 6,180,672 B1 | 1/2001 | Lichtenberg et al. ........ 514/561 |
| 6,274,199 B1 * | 8/2001 | Preston et al. ............... 427/298 |
| 6,340,384 B1 * | 1/2002 | Walker ...................... 106/18.32 |
| 6,375,727 B1 * | 4/2002 | Walker ...................... 106/18.32 |
| 6,395,698 B1 | 5/2002 | Daun et al. .................. 510/384 |
| 6,416,789 B1 | 7/2002 | Marks et al. ................ 424/641 |

FOREIGN PATENT DOCUMENTS

| CA | 1 174 005 | 9/1984 | .......... A01N/31/14 |
|---|---|---|---|
| DE | 3743 821 A1 | 7/1989 | ............ B27K/3/34 |
| DE | 4217 882 A1 | 12/1993 | .......... A01N/55/04 |
| DE | 44 41 674 A1 | 5/1996 | ......... C07C/275/32 |
| DE | 196 40 874 A | 4/1998 | |
| DE | 196 40 874 | 4/1998 | ............ B27K/3/34 |
| DE | 196 48 888 A1 | 5/1998 | ............ B27K/3/50 |
| EP | 0 370 182 | 5/1990 | ............ B27K/3/50 |
| EP | 0 381 482 | 8/1990 | ............ B27K/3/50 |
| EP | 0 482 961 A | 4/1992 | |
| EP | 0 571 846 A1 | 12/1993 | .......... A01N/47/12 |
| JP | 57022003 | 2/1982 | ............ B27K/3/52 |
| JP | 64-1796 | 1/1989 | ............ C11D/3/28 |
| JP | 1-268605 | 10/1989 | .......... A01N/33/24 |
| JP | 09 059672 A | 3/1997 | |
| WO | 97/01423 | 1/1997 | ............ B27K/3/50 |
| WO | 98/00008 | 1/1998 | .......... A01N/25/02 |
| WO | 98/18321 | 5/1998 | .......... A01N/25/30 |
| WO | 98/31518 | 7/1998 | ............ B27K/3/00 |
| WO | WO 00 71314 A | 11/2000 | |

OTHER PUBLICATIONS

American Wood Preservers' Association, P5–Waterborne Preservatives, 4–5, 1998.
Encyclopedia of Chemical Technology, vol. 2, pp. 259–271, John Wiley & Sons Inc., 1978.
Archer et al., Forest Products Journal, 45(1):86–89, Jan. 1995.
Hirobumi et al., 120:301698 1993 (abstract).
Liu et al., 25$^{th}$ Annual Meeting of the International Research Group on Wood Preservation, Nusa Dua Bali, Indonesia, May 29, 1994–Jun. 3, 1994.
Nicholas et al., 28$^{th}$ Annual Meeting of the International Research Group on Wood Preservation, Whistler, Canada, May 25, 1997–May 30, 1997.
Williams et al., American Wood–Preservers' Association, 90:156–176, 1994.

\* cited by examiner

Primary Examiner—Joseph D. Anthony
(74) Attorney, Agent, or Firm—Darby & Darby

(57) ABSTRACT

The present inventors have discovered that amine oxides are highly effective as wood preservatives. The present invention provides a wood preservative composition comprising a biocidally effective amount of one or more amine oxides. Preferably, the wood preservative composition is substantially free of halogenated compounds (such as halides and chlorinated compounds) and quaternary ammonium compounds. The wood preservative composition of the present invention exhibits low toxicity, high stability in water, low corrosivity to metal substrates (such as steel substrates), excellent penetration and uniform distribution into wood, low odor, waterproofing properties, and high leaching resistance. The wood preservative composition may be applied to the surface of a wood substrate or be applied by pressure treating the wood substrate with the wood preservative composition. Other cellulosic and fiber materials, such as cotton, burlap, and like materials, may be preserved with the composition of the present invention. Another embodiment is a method of controlling microorganisms, such as fungal decay organisms (generally known as white rot, brown rot, and soft rot fungi) and sapstain organisms, on and/or in a wood substrate, such as fresh cut lumber, comprising applying a biocidally effective amount of the composition of the present invention to the wood substrate.

20 Claims, No Drawings

AMINE OXIDE WOOD PRESERVATIVES

This application claims the benefit of U.S. Provisional Application Ser. No. 60/285,863, filed Apr. 23, 2001, and U.S. Provisional Application Ser. No. 60/206,751, filed May 24, 2000.

FIELD OF THE INVENTION

This invention relates to a wood preservative composition comprising a biocidally effective amount of at least one amine oxide and a method of controlling microorganisms in a wood substrate or other cellulosic or fiber material with the wood preservative composition. This invention also relates to a method of removing algae from a substrate with one or more amine oxides.

BACKGROUND OF THE INVENTION

Wood is an important building and construction material that is used in a variety of applications, such as housing material, utility poles, and railroad ties. Effective wood preservatives and waterproofing compounds that improve dimensional stability are necessary to maintain the integrity of these structures.

Quaternary alkyl ammonium compounds (QAC's), such as didecyldimethylammonium chloride (DDAC), have been shown to be effective as fungicides. However, QAC's do not readily penetrate and uniformly distribute into wood. Because of the poor penetration and distribution, certain areas of the wood do not receive adequate protection, often resulting in the wood rotting from the inside out. Furthermore, DDAC corrodes steel tanks and other metal components commonly used in wood treatment systems.

U.S. Pat. No. 4,357,163 discloses a chlorinated phenol wood treating composition containing a chlorophenol, a fatty acid amine oxide, and water. The amine oxide was included to increase penetration of the chelating agents and chlorophenols into the wood and to stabilize the chlorophenol in water.

U.S. Pat. No. 5,833,741 discloses a waterproofer wood preservative system comprising a waterproofing enhancing amount of waterproofer composition and a biocidally effective amount of a biocide. The waterproofer is an alkyl dimethyl amine oxide, an alkyl acetoacetate, or a waterproofing quaternary ammonium compound. The biocide comprises at least one biocidal quaternary ammonium compound. Generally, the concentration of biocide in the waterproofer wood preservative system is 0.25 to 4% by weight.

U.S. Pat. Nos. 3,296,145 and 3,484,523 disclose a composition for cleaning, softening, and sanitizing fabrics; cleaning and sanitizing walls and floors; and cleaning and degerming human skin and similar organic tissue. The composition contains a quaternary alkyl ammonium compound and a tertiary amine oxide.

U.S. Pat. No. 4,179,504 discloses alkyl amine oxides which are effective as ectoparasiticidal and ovicidal toxicants and their use in shampoos.

Devinsky et al., Chemical Abstracts 103:122986s (1 986), disclose certain N,N'-didecyl-N,N'-dimethyl-α,ω-alkanediamine dioxides which inhibit the growth of bacteria and fungi.

Societe de Produits Chimiques et de Synthese, Chemical Abstracts 84849c (1966), discloses that dimethyl-laurylamine oxide, bis(β-hydroxyethyl)laurylamine oxide, and dimethylsoyaamine oxide were used for suppressing the growth of some dermal fungi or bacteria, such as *C. perfringens, S. anaerobius,* and *A. niger.*

However, prior to the present invention, there was no indication that amine oxides would be effective as wood preservatives. In fact, their inclusion in wood treating solutions was to either stabilize a preservative ingredient, such as chlorophenol as in U.S. Pat. No. 4,357,163, or act as a waterproofer in conjunction with a preservative ingredient, as in U.S. Pat. No. 5,833,741.

In light of the foregoing, it is desirable to have a wood preservative that has broad antifungal activity, low toxicity to non-target organisms, high phase stability in water, and low corrosivity.

SUMMARY OF THE INVENTION

The present inventors have discovered that amine oxides are highly effective as wood preservatives. The present invention provides a wood preservative composition comprising a biocidally effective amount of one or more amine oxides. Preferably, the wood preservative composition is substantially free of halogenated compounds (such as halides and chlorinated compounds) and quaternary ammonium compounds. The wood preservative composition of the present invention exhibits low toxicity, high stability in water, low corrosivity to metal substrates (such as steel substrates), excellent penetration and uniform distribution into wood, low odor, waterproofing properties, and high leaching resistance. The wood preservative composition may be applied to the surface of a wood substrate or be applied by pressure treating the wood substrate with the wood preservative composition. Other cellulosic and fiber materials, such as cotton, burlap, and like materials, may also be preserved with the composition of the present invention.

Another embodiment is a method of controlling microorganisms, such as fungal decay organisms (generally known as white rot, brown rot, and soft rot fungi) and sapstain organisms (e.g. stains, mold, and fungi) on and/or in a wood substrate, such as fresh cut lumber, comprising applying a biocidally effective amount of the composition of the present invention to the wood substrate.

Yet another embodiment is a method of controlling sapstain organisms and/or fungi (including mold) on and/or in a wood substrate, such as fresh cut lumber, comprising applying a sapstain and/or fungicidally (mold) inhibiting effective amount of one or more amine oxides and one or more phosphonic iron stain inhibitors.

Yet another embodiment of the present invention is a wood preservative system comprising a wood substrate and a biocidally effective amount of one or more amine oxides. Preferably, the wood substrate comprises a fungicidally or sapstain inhibiting effective amount of one or more amine oxides.

DETAILED DESCRIPTION OF THE INVENTION

The present invention provides a wood preservative composition comprising a biocidally effective amount of one or more amine oxides. The composition of the present invention exhibits high penetration and uniform distribution into wood substrates as well as low corrosivity to metal substrates and high leaching resistance.

The amine oxide may be a trialkylamine oxide, an alkylcyclicamine oxide, a dialkylpiperazine di-N-oxide, an alkyldi(poly(oxyalkylene))amine oxide, a dialkylbenzylamine oxide, a fatty acylamidopropyldimethylamine oxide, a diamine dioxide; a triamine trioxide, or any combination of any of the foregoing.

Preferred trialkylamine oxides have the formula $R^1R^2R^3N \rightarrow O$, where $R^1$ is a linear, branched, cyclic or any combination thereof $C_8$ to $C_{40}$ saturated or unsaturated group; and $R^2$ and $R^3$ independently are linear, branched, or any combination thereof $C_1$ to $C_{40}$ saturated or unsaturated groups. $R^1$, $R^2$, and $R^3$ independently may be alkyl, alkenyl, or alkynyl groups. More preferably, $R^1$ is a linear, branched, cyclic or any combination thereof $C_8$ to $C_{22}$ saturated or unsaturated group, such as coco, hydrogenated tallow, soya, decyl, and hexadecyl; and $R^2$ and $R^3$ independently are linear, branched, or any combination thereof $C_1$ to $C_{22}$ saturated or unsaturated groups, such as coco, hydrogenated tallow (which is typically about 70–75% by weight of $C_{18}$ alkyl, about 20–25% by weight of $C_{16}$ alkyl, and traces of lower derivatives), soya, decyl, and hexadecyl.

A preferred trialkylamine oxide is a dialkylmethylamine oxide having the formula $R^1R^2CH_3N{\rightarrow}O$, where $R^1$ and $R^2$ are defined as above. Another preferred trialkylamine oxide is an alkyldimethylamine oxide having the formula $R^1(CH_3)_2N{\rightarrow}O$, where $R^1$ is defined as above. More preferred alkyldimethylamine oxides have the formula $R^{19}(CH_3)_2N{\rightarrow}O$, where $R^{19}$ is a linear or branched $C_8$–$C_{18}$ alkyl. Preferably, $R^{19}$ is a linear or branched $C_{10}$–$C_{16}$ alkyl. Alkyldimethylamine oxides are non-toxic and non-mutagenic surfactants. Suitable alkyldimethylamine oxides include, but are not limited to, decyldimethylamine oxide, cocodimethylamine oxide, dodecyldimethylamine oxide, a $C_{10}$–$C_{14}$ alkyldimethylamine oxide, hexadecyldimethylamine oxide, a $C_{16}$–$C_{18}$ alkyldimethylamine oxide, and any combination of any of the foregoing. A more preferred wood preservative composition contains a mixture of dodecyl dimethyl amine oxide and hexadecyl dimethyl amine oxide.

Preferred alkylcyclicamine oxides have the formula $R^4R^5R^6N{\rightarrow}O$ where $R^4$ is defined as $R^1$ above and $R^5$ and $R^6$ are linked to form a cyclic group. The cyclic group typically contains from 4 to 10 carbon atoms and may optionally contain oxygen, sulfur, nitrogen, or any combination of any of the foregoing. More preferred alkylcyclicamine oxides include, but are not limited to, an alkylmorpholine N-oxide, a dialkylpiperazine di-N-oxide, and any combination of any of the foregoing.

Preferred alkylmorpholine N-oxides have the formula

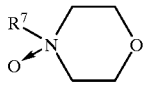

where $R^7$ is defined as $R^1$ above. According to a more preferred embodiment, $R^7$ is a linear or branched $C_{10}$ to $C_{16}$ alkyl. Examples of preferred alkylmorpholine N-oxides include, but are not limited to, cetyl morpholine N-oxide and lauryl morpholine N-oxide.

Preferred dialkylpiperazine di-N-oxides have the formula

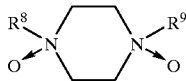

where $R^8$ is defined as $R^1$ above and $R^9$ is defined as $R^2$ above.

Preferred alkyldi(poly(oxyalkylene))amine oxides have the formula

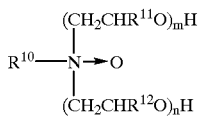

where $R^{10}$ is defined as $R^1$ above; $R^{11}$ and $R^{12}$ independently are H or $CH_3$; and m and n independently are integers from about 0 to about 10 and at least one of m and n is greater than 0.

Preferred dialkylbenzylamine oxides have the formula $R^{13}R^{14}R^{15}N{\rightarrow}O$, where $R^{13}$ is defined as $R^1$ above; $R^{14}$ is defined as $R^2$ above; and $R^{15}$ is benzyl. More preferred dialkylbenzylamine oxides include, but are not limited to, alkylbenzylmethylamine oxides having the formula $R^{13}R^{15}CH_3N{\rightarrow}O$ where $R^{13}$ and $R^{15}$ are defined as above. According to a more preferred embodiment, $R^{13}$ is a linear or branched $C_8$–$C_{12}$ alkyl.

Preferred fatty acylamidopropyldimethylamine oxides have the formula

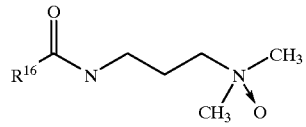

where $R^{16}$ is defined as $R^1$ above.

Preferred diamine oxides have the formula

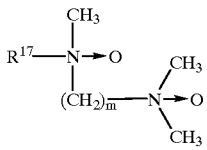

where $R^{17}$ is defined as $R^1$ above; and m is an integer from about 1 to about 10.

Preferred triamine oxides have the formula

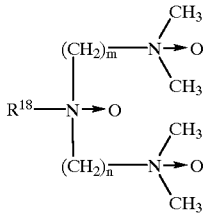

where $R^{18}$ is defined as $R^1$ above; and m and n independently are integers from about 1 to about 10.

Long chain ($C_{16}$ or greater) amine oxides, such as hexadecylamine oxides and hydrogenated tallow amine oxides, are particularly preferable for imparting waterproofing properties to the composition. Short chain ($C_{14}$ and shorter) amine oxides aide are water soluble and aide in solubilizing long chain amine oxides and are typically better preservatives.

A blend of long chain and short chain amine oxides is contemplated in one embodiment of the present invention. The long chain amine oxides are generally blended with the short chain amine oxides at a weight ratio of from about 5:1 to about 1:5 and preferably at a weight ratio of from about 2:1 to about 1:1.

According to a preferred embodiment, the composition contains a mixture of $C_{16}$–$C_{18}$ long chain amine oxides to impart waterproofing properties and $C_{10}$–$C_{14}$ short chain amine oxides to solubilize the long chain amine oxides. A particularly preferable blend is a mixture of hexadecyldimethylamine oxide and dodecyldimethylamine oxide at a weight ratio of about 5:2.

The wood preservative composition comprises a biocidally effective amount of one or more amine oxides. Preferably, the composition comprises a fungicidally effective amount and more preferably a sapstain inhibiting effective amount of one or more amine oxides.

The wood preservative composition can be used to prevent the growth of sapstain (e.g. stains, mold, and fungi) on fresh cut timber between the time the timber is cut into board and the time when the board has dried to a low moisture content.

An aqueous composition of the present invention generally contains from about 0.1 to about 5%, preferably from about 0.25 to about 3%, and more preferably from about 0.5 to about 1.5% by weight of amine oxide, based upon 100% total weight of wood preservative composition. For application to pressure treated wood, the composition preferably contains from about 0.1 to about 5% and more preferably from about 0.25 to about 3% by weight of amine oxide, based upon 100% total weight of wood preservative composition. For controlling sapstain, the wood preservative composition preferably contains from about 0.1 to about 5% and more preferably from about 0.5 to about 1% by weight of amine oxide, based upon 100% total weight of wood preservative composition.

According to a preferred embodiment, the wood preservative composition comprises a waterproofing and biocidally, fungicidally, or sapstain inhibiting effective amount of one or more amine oxides.

The wood preservative composition of the present invention may further comprise a solvent, such as water, a water miscible solvent, or a combination thereof. Suitable water miscible solvents include, but are not limited to, alcohols, glycols, esters, ethers, polyethers, amines, ketones, and any combination of any of the foregoing. Preferably, the solvent is water.

The wood preservative composition may also comprise further auxiliaries, such as corrosion inhibitors, iron stain inhibitors, wetting agents, adhesives, emulsifiers, fillers, carriers, viscosity and pH regulators, binders, tackifiers, other active ingredients (such as other biocidally active ingredients), and any combination of any of the foregoing.

Suitable iron stain inhibitors include, but are not limited to, phosphonic iron stain inhibitors, such as aminotri (methylenephosphonic acid), 1-hydroxyethylidene-1,1-diphosphonic acid, diethylenetriaminepenta (methylenephosphonic acid), bis-(hexamethylene)triamine phosphonic acid, and any combination of any of the foregoing. The inventors have discovered that the inclusion of a phosphonic iron stain inhibitor, such as 1-hydroxyethylidene-1,1-diphosphonic acid and bis-(hexamethylene)triamine phosphonic acid, improves the biological efficacy of the amine oxide. Furthermore, since many iron stain inhibitors are highly acidic, prior art treating solutions containing them typically have a pH of less than 2. In contrast, wood preservative compositions of the present invention which contain iron stain inhibitors typically have a pH ranging from about 3 to about 7.

Other adjuvants may be included in the composition as known to one of ordinary skill in the art.

Generally, the wood preservative composition is neutral, i.e., has a pH of from about 6 to about 8.

According to a preferred embodiment, the wood preservative composition is substantially free (i.e., contains less than 0.1% by weight) of quaternary ammonium compounds, halogenated compounds (including halides and chlorinated compounds such as chlorophenols), or both. More preferably, the wood preservative composition contains less than 0.01, 0.001, or 0.0001% by weight of quaternary ammonium compounds, halogenated compounds (including chlorine containing compounds such as chlorophenols), or both. Most preferably, the wood preservative composition is free of quaternary ammonium compounds, halogenated compounds (including chlorine containing compounds such as chlorophenols), or both.

According to another preferred embodiment, the wood preservative composition is substantially free (i.e., contains less than 0.1% by weight) of biocides, bactericides, or fungicides other than amine oxides. More preferably, the wood preservative composition contains less than 0.01, 0.001, or 0.0001% by weight of biocides, bactericides, or fungicides other than amine oxides. Most preferably, the wood preservative composition is free of biocides, bactericides, or fungicides other than amine oxides.

A particularly preferable sapstain inhibiting composition of the present invention comprises cocodimethylamine oxide and, optionally, an iron stain inhibitor. Also, special mention is made of cocodimethylamine oxide alone or in combination with hexadecyldimethylamine oxide as a preservative for use in pressure treating lumber.

The wood preservative composition may be applied to any wood substrate, such as any hard wood or soft wood, to present sapstain. Typically, for preventing or controlling sapstain and mold, the wood preservative composition is applied to green wood. The term "green" as used herein is defined as freshly cut, unseasoned, or the like. Examples of suitable wood substrates include, but are not limited to, maple, oak, birch, cherry, fir, and the like. The wood preservative composition may be applied to any wood substrate which is to be pressure treated. Preferably, the wood substrate is a soft wood, such as a pine, fir, or hemlock. Suitable pine wood substrates include, but are not limited to, southern yellow pine and ponderosa pine. More, preferably, the wood substrate is southern yellow pine.

Methods of applying the wood preservative composition include, but are not limited to, spraying, soaking, immersing, vacuum impregnation, pressure treatment, brushing, and the like. Preferably, the substrate is immersed in the wood preservative composition of the present invention or the substrate is pressure treated with the composition.

The composition may be prepared by dissolving the amine oxide and adjuvants in water. The mixture may be heated to a temperature of from about 50 to about 60° C. and/or stirred to expedite mixing. For example, a 30% (w/w) mixture of hexadecyl dimethyl amine oxide, available as Barlox® 16S from Lonza Inc. of Fair Lawn, N.J., which is a paste, may be mixed with a 30% (w/w) aqueous solution of coco-dimethylamine oxide and water to form a concentrated solution suitable for producing use dilutions of the wood preservative composition.

A wood substrate containing the wood preservative composition generally comprises from about 0.1 to about 5% by weight, preferably from about 0.25 to about 3% by weight, and more preferably from about 0.5 to about 2% by weight of amine oxide, based upon 100% total weight of preserved wood substrate.

Another embodiment is a method of controlling microorganisms, such as fungi and sapstain organisms, on and/or in a wood substrate comprising applying a biocidally effective amount of the wood preservative composition of the present invention to the wood substrate. The term "controlling" as used herein includes, but is not limited to, inhibiting the growth of microorganisms, such as fungi and sapstain organisms. Non-limiting examples of fungi are *Trametes versicolor* (*T. versicolor*), *Gloeophyllum trabeum* (*G. trabeum*), *Poria placenta* (*P. placenta*), *Lentinus lepideus* (*L. lepideus*), *Coniophoraputeana* (*C. puteana*), and *Chaetomium globsum* (*C. globsum*).

According to a preferred embodiment, the wood preservative composition further comprises one or more iron stain inhibitors, preferably phosphonic iron stain inhibitors, is applied to a wood substrate to control sapstain organisms. Generally, the composition contains from about 0.05 to about 1% by weight of phosphonic iron stain inhibitor, based upon 100% by weight of composition. Preferably, the composition contains from about 0.1 to about 0.5 and more preferably from about 0.15 to about 0.3% by weight of phosphonic iron stain inhibitor, based upon 100% by weight of composition.

DESCRIPTION OF THE PREFERRED EMBODIMENTS

The following examples illustrate the invention without limitation. All parts and percentages are given by weight unless otherwise indicated. All Barlox® ingredients are available from Lonza Inc. of Fair Lawn, N.J.

EXAMPLE 1

A concentrate of a wood preservative composition was prepared as follows. 50 parts of Barlox® 16S, about 20 parts of Barlox® 12, and about 80 parts water were mixed. Barlox® 16S is an aqueous solution containing 30% by weight of hexadecyldimethylamine oxide. Barlox® 12 is an aqueous solution containing 30% by weight of coco-dimethylamine oxide. The mixture was heated and/or allowed to sit until a clear solution was obtained, e.g., by about 40 to 50° C. for about 2 to 4 hours or simply sitting at room temperature overnight. The resulting composition was clear.

EXAMPLE 2

The wood preserving efficacy of each aqueous test solution in Table 1 below was tested on freshly cut white birch wood as follows. All percentages in Table 1 are by weight. A branch of white birch tree measuring about 3 inches in diameter was cut into pieces about 6 inch in length. Each piece was then split into 4 sections. Each section was dipped into the test solution for about 1 minute and blotted with a paper towel to remove excess liquid. The sections were sealed in a clear plastic bag and stored at ambient conditions. The sections were observed after 1, 3, 7, and 12 weeks for the growth of stains, molds, and fungi. The aqueous test solutions were prepared by mixing the active ingredient with water. The results are shown in Table 1.

TABLE 1

| Test solution | Rating* of treated white birch sections vs. Time | | | |
|---|---|---|---|---|
| | 1 week | 3 weeks | 7 weeks | 12 weeks |
| None | 4 | 1 | 1 | — |
| Water | 3 | 2 | 1 | — |
| 1% Didecyldimethyl ammonium chloride | 4 | 4 | 3 | 3 |
| 1% Coco-dimethyl amine oxide | 4 | 4 | 3 | 2 |
| 1% Tetradecyl dimethylamine oxide | 4 | 3 | 2 | 2 |
| 1% Decyl dimethylamine oxide | 3 | 2 | 2 | 2 |
| 1% Hexadecyl dimethylamine oxide | 3 | 2 | 2 | 2 |
| 0.5% Hexadecyl dimethylamine oxide and 0.5% dodecyldimethyl amine oxide | 4 | 3 | 3 | 3 |

*Rating scale:
4 - Clean with no visible stain or mold
3 - Trace amount of white/black fungal growth
2 - Black and/or white fungal growth visible on all faces and ends
1 - Heavy fungal growth

EXAMPLE 3

The wood preserving efficacy of each aqueous test solution in Table 2 below was tested on freshly cut green chestnut oak as described in Example 2. All percentages in Table 2 are by weight. The sections were observed after 2, 4, 5, and 9 weeks for the growth of stains, molds, and fungi. The results are shown in Table 2. The aqueous test solutions were prepared by mixing the active ingredient with water.

TABLE 2

| Test solution | Rating of treated green chestnut oak sections vs. Time | | | |
|---|---|---|---|---|
| | 2 weeks | 4 weeks | 5 weeks | 9 weeks |
| None | 1 | 1 | | |
| Water | 2 | 2 | 1 | |
| 0.25% 1-Hydroxyethylidene-1,1-diphosphonic acid (HEDP)[1] | 2 | 2 | 1 | 1 |
| 1% Didecyldimethyl ammonium chloride | 3 | 2 | 2 | 1 |
| 1% Dodecyl dimethylamine oxide | 3 | 2 | 2 | 1 |
| 1% Dodecyl dimethylamine oxide and 0.25% HEDP | 4 | 4 | 3 | 1 |
| 1% Dodecyl dimethylamine oxide and 0.2% bis-(hexamethylene)triamine phosphonic acid[2] | 4 | 4 | 3 | 2 |
| 1% Didecyldimethyl ammonium chloride and 0.25% HEDP | 3 | 2 | 1 | 1 |

[1]1-Hydroxyethylidene-1,1-diphonic acid (HEDP) is available as Unihib ® 106 from Lonza Inc. of Fair Lawn, NJ.
[2]Bis-(hexamethylene)triamine phosphonic acid is available as Unihib ® 1704 from Lonza Inc. of Fair Lawn, NJ.

The pH of the 1% didecyldimethyl ammonium chloride and 0.25% HEDP solution was about 1.9 while the pH of the 1% dodecyl amine oxide and 0.25% HEDP solution was about 4.8.

EXAMPLE 4

The efficacy of aqueous solutions of amine oxides and didecyldimethyl ammonium chloride to inhibit fungus growth was evaluated by the agar plate method known in the art. The concentration ($IC_{50}$) of each aqueous solution at which 50% retardation of the growth of the fungi is observed was determined. The fungi tested were *Trametes versicolor* (*T. versicolor*), a white rot fungus; *Gloeophyllum trabeum* (*G. trabeum*), a brown rot fungus which is tolerant of arsenic and phenolic type wood preservatives; *Poria placenta* (*P. placenta*), a brown rot fungus which is tolerant to copper in wood preservatives; *Lentinus lepideus* (*L. lepideus*), a brown rot fungus which is tolerant to creosote; *Coniophora puteana* (*C. puteana*), a brown rot fungus; and *Chaetomium globsum* (*C. globsum*), a soft rot fungus. The results are shown in Tables 3A and 3B below.

TABLE 3A

| Aqueous Test Solution | $IC_{50}$ (ppm) | | |
|---|---|---|---|
| | *T. versicolor* | *G. trabeum* | *P. placenta* |
| Octyldimethylamine oxide | 800 | 250–400 | 300 |
| Decyldimethylamine oxide | 300–500 | 20–40 | 15–25 |
| Coco-dimethylamine oxide | 40–50 | 10–15 | 3–7 |
| Tetradecyl dimethylamine oxide | 70 | 15–25 | 2–5 |
| Hexadecyl dimethylamine oxide | 30 | 25–30 | 5–25 |
| Octadecyl dimethylamine oxide | 800 | 250 | 20–50 |
| Mixture of hexadecyl dimethyl-amine oxide and coco-dimethyl-amine oxide at a 5:2 weight ratio | 10 | 4 | 3 |
| Didecyldimethyl ammonium chloride | 30–50 | 10–40 | 5–25 |

TABLE 3B

| Aqueous Test Solution | IC$_{50}$ (ppm) | | |
|---|---|---|---|
| | L. lepideus | C. puteana | C. globsum |
| Octyldimethylamine oxide | — | — | 400 |
| Decyldimethylamine oxide | — | — | 50–100 |
| Coco-dimethylamine oxide | 15 | 80 | 50–70 |
| Tetradecyl dimethylamine oxide | — | — | 80–100 |
| Hexadecyl dimethylamine oxide | 3 | 80 | 20–50 |
| Octadecyl dimethylamine oxide | — | — | 600 |
| Mixture of hexadecyl dimethyl-amine oxide and coco-dimethyl-amine oxide at a 5:2 weight ratio | 10 | 3 | 10 |
| Didecyldimethyl ammonium chloride | — | — | 10–20 |

EXAMPLE 5

The aqueous test solutions in Table 4 below were prepared and tested as follows.

Wafers about ¼ inch thick were cut from southern yellow pine board and placed in a vacuum desiccator. The vacuum pressure was maintained at about −80 kPa for about 15 minutes. Test solutions listed in Table 4 were injected into the vacuum. Vacuum was broken by the addition of air and the board was allowed to stand for about 10 minutes. Excess solution was blotted from the wafers. The wafers were returned to the desiccator and another vacuum was drawn to about −80 kPa pressure for about 15 minutes to remove any kickback solution.

Leaching in Water

About 10 g of the test solution treated wafers were vacuum impregnated with about 200 g of water and soaked in water for about 5 days with occasional shaking. After the 5 days, the concentration of preservative in the water and in the wafers was determined. The concentration of preservative in the water was determined by American Wood-Preserver's Association Standard No. A18-99. The concentration of preservative in the wood was determined by the high performance liquid chromatography method described in American Wood-Preserver's Association Standard No. A16-93.

Leaching in Water and Soil

About 10 g of the test solution treated wafers and about 10 g of air dry organic forest soil were vacuum impregnated with about 150 g water, slowly agitated for about 5 days, and separated. After the 5 days, the concentration of preservative in the soil and in the wafers was determined as described above.

The results are shown in Table 4.

TABLE 4

| | Wafer treated with Water | | Wafer treated with Water and Soil | |
|---|---|---|---|---|
| Aqueous Test Solution | Concentration of Preservative in Wafer after 5 days (% w/w) | Concentration of Preservative in Water after 5 days (ppm) | Concentration of Preservative in Wafer after 5 days (% w/w) | Concentration of Preservative in Soil after 5 days (% w/w) |
| 1.5% Didecyldimethyl ammonium chloride | 1.5 | 40 | 1.1 | 0.4 |
| 1.5% Octadecylbenzyl dimethyl ammonium chloride | 2.0 | 50 | 1.3 | 0.1 |
| 1.5% Dodecyldimethyl-amine oxide | 1.5 | 90 | 0.7 | 05 |
| 1% Dodecyldimethyl amine oxide and 0.5% decyldimethyl amine oxide | 1.5 | 140 | 0.7 | 05 |

EXAMPLE 6

Southern yellow pine (SYP) lumber pieces were pressure treated to assess penetration of amine oxides. An aqueous test solution containing 1.7% by weight of hexadecyl dimethylamine oxide (hexadecyl DMAO) and 0.6% by weight of dodecyl dimethylamine oxide (dodecyl DMAO) was prepared. Two 2' pieces of kiln dried #1 grade SYP 2×4's were end coated with an epoxy paint. The wood pieces were placed in a pressure treating cylinder for about 30 minutes at about −90 kPa, injected with the aqueous test solution, and pressurized to about 950 kPa for about 30 minutes. The pressure was released by the addition of air, the solution was drained, and the wood pieces were exposed to a vacuum of about −90 kPa for about 30 minutes. After air drying, the pieces were cut in the middle and several ¼" wafers were removed from the outer 0.3", second 0.3", and inner 0.3". The wafers were analyzed by HPLC to determine the concentration of amine oxide in the wafers.

The results are shown in Table 5.

TABLE 5

| Piece | Preservative | Retention (%) Target | Retention (%) Actual | Amine Oxide found in zones (%) Outer 3" | Amine Oxide found in zones (%) Second 3" | Amine Oxide found in zones (%) Inner 3" |
|---|---|---|---|---|---|---|
| #1 | Hexadecyl DMAO | 1.9 | 2.3 | 2.9 | 2.0 | 1.7 |
|  | Dodecyl DMAO | 0.7 | 1.1 | 2.4 | 1.4 | 0.8 |
| #2 | Hexadecyl DMAO | 1.7 | 2.0 | 2.5 | 2.1 | 2.1 |
|  | Dodecyl DMAO | 0.6 | 0.8 | 2.0 | 1.2 | 1.1 |

EXAMPLE 7

Wafers were prepared as described in Example 5 with the aqueous treatment solution described in Example 6 and with an aqueous solution containing 1% (w/w) of didecyldimethyl ammonium chloride (DDAC). The samples were shaken for 7 days instead of the 5 days described in Example 5. The results are shown in Table 6.

TABLE 6

| Sample | Concentration of Preservative in Unleached Wood after 7 days (% w/w) | Concentration of Preservative in after 7 days (% w/w) | Concentration of Preservative in Water after 7 days (ppm) | Concentration of Preservative in Wafer after 7 days (% w/w) | Concentration of Preservative in Soil after 7 days (% w/w) |
|---|---|---|---|---|---|
| Hexadecyl-DMAO | 2.3 | 2.6 | <10 | 1.5 | 0.33 |
| Dodecyl-DMAO | 1.1 | 1.7 | <10 | 0.5 | 0.15 |
| DDAC | 1.25 | 1.24 | <10 | 0.95 | 0.5 |

EXAMPLE 8

Southern yellow pine lumber pieces were pressure treated with an aqueous solution containing hexadecyldimethylamine oxide and dodecyldimethylamine oxide by the procedure described in Example 6. Two pieces were treated with an aqueous solution containing 1.65% by weight of hexadecyldimethylamine oxide and 0.6% by weight of dodecyldimethylamine oxide and two pieces were treated with an aqueous solution containing 0.8% by weight of hexadecyldimethylamine oxide and 0.3% by weight of dodecyldimethylamine oxide. The treated pieces were placed outside on a rack and the effect of natural weathering was observed after 2, 6, and 10 months.

This procedure was repeated with aqueous solutions containing 0.5% or 1% by weight of copper chromium arsenate or 0.5% or 1% by weight of didecyldimethyl ammonium chloride.

Four pieces were treated with water (untreated lumber pieces) and tested as described above.

The results are shown in Table 7.

TABLE 7

| Test Solution | Observations After 2 Months | Observations After 6 Months | Observations After 10 Months |
|---|---|---|---|
| Untreated | Generally darker surface with sections quite dark. A new crack developed on one piece. | The pieces were darker overall, had many cracks, and a wet appearance. | The pieces were dark black with numerous cracks. |
| Hexadecyldimethylamine oxide (1.65 and 0.8%) and dodecyldimethylamine oxide (0.6 and 0.3%) | All four pieces clean, clear, and unchanged from the start. | Two of the four pieces were clean and clear. The other two pieces had darker sections and fine cracks. | All four pieces were a uniform light gray color and had some cracks. |
| Copper chromium arsenate (0.5 and 1%) | General covering of small dark spots. Surface integrity is unchanged. | Small mildew spots and many small cracks were present in all four pieces | The pieces were brownish with brown and black spots and many cracks |
| Didecyldimethyl ammonium chloride (0.5 and 1%) | Few spots and darker black sections covering two of the four pieces. A crack developed in one of the pieces | Three of the four pieces had dark sections and many cracks. | The pieces were a gray black color with many cracks. |

EXAMPLE 9

The corrosivity of each aqueous amine oxide solution and each aqueous didecyldimethyl ammonium chloride solution in Table 8 and water on steel substrates was determined as follows. A carbon steel coupon was submerged into the aqueous solution so that the coupon was about ¾ covered and stored for two weeks. The coupon was shaken occasionally so that the top of the coupon was wetted periodically. After two weeks, the coupon was weighed to determine the amount of steel corroded and the surface of the coupon was observed. The results are shown in Table 8.

TABLE 8

| Test Solution | Weight Lost (%) | Observations |
|---|---|---|
| Water | 0.28 | Solution is rust colored. Coupon is rusted. |
| 0.3% didecyldimethyl ammonium chloride | 0.44 | Black corrosion |
| 1% didecyldimethyl ammonium chloride | 0.40 | Black corrosion |
| 1% hexadecyl dimethylamine oxide | −0.02[1] | Coupon and solution both clear |
| 1% decyl dimethylamine oxide | −0.02 | Coupon and solution both clear |
| 1% decyl dimethylamine oxide and 0.1% ammonia | −0.01 | Coupon and solution both clear |
| 1% decyl dimethylamine oxide and 0.1% acetic acid (the pH of the solution was 5.1) | 0.4 | Orange rust |
| 1% decyl dimethylamine oxide and 0.01% acetic acid (the pH of the solution was 6.7) | 0.01 | Coupon and solution both clear |
| 1% decyl dimethylamine oxide and 0.1% lauric acid (the pH of the solution was 6.7) | 0.01 | Coupon and solution both clear |

[1]A negative weight loss means a gain in weight.

EXAMPLE 10

Ponderosa pine wafers and southern yellow pine sticks were treated with the aqueous test solutions shown in Tables 9–12 by the procedures described above to determine their waterproofing efficacy. The treated wafers and sticks were air dried and weathered for up to 700 days. A water uptake test was performed to determine the water resisting efficacy of each wafer or stick. The water uptake was determined by air drying the wafer or stick to a constant weight, immersing the wafer or stick in water for 30 minutes, weighing the wafer or stick, and calculating the water uptake. The percentage water resisting efficiency (% WRE) was determined by the following formula:

% WRE=100*(Weight of Immersed Treated Wood−Weight of Immersed Untreated Wood)/(Weight of Immersed Untreated Wood)

The weight of the immersed untreated wood was measured after 30 minutes and used as the control. The results are shown in Tables 9–12 below.

TABLE 9

Water Uptake (%) of Weathered Ponderosa Pine Wafers

| Test solution | Day 0 | % WRE Start (Day 0) | Day 170 | Day 330 | Day 690 |
|---|---|---|---|---|---|
| Control (Untreated) | 58 | — | 104 | 154 | 161 |
| Thompson's Waterseal ™* | 11 | 87 | 13 | 43 | 119 |
| 1% Didecyldimethyl ammonium chloride | 58 | 33 | 73 | 87 | 107 |
| 1%hexadecyl dimethylamineoxide | 35 | 60 | 51 | 77 | 89 |

*Thompson's Waterseal is available from Thompson and Formby of Memphis, TN.

TABLE 10

Water Uptake (%) of Weathered Ponderosa Pine Wafers

| Test solution* | Day 0 | Day 105 | Day 430 |
|---|---|---|---|
| Untreated | 47 | 64 | 124 |
|  | 48 | 63 | 123 |
| 1% Didecyldimethyl ammonium chloride | 35 | 56 | 71 |
|  | 38 | 58 | 80 |
| 1.5% hexadecyl dimethylamine oxide and 0.6% dodecyl dimethylamine oxide | 16 | 23 | 38 |
|  | 17 | 25 | 38 |
| 0.4% Didecyldimethyl ammonium chloride and 0.6% HT-AO[1] | 16 | 29 | 53 |
|  | 18 | 41 | 60 |

*Each testing solution was tested twice, yielding two sets of test results.
[1]HT-AO is hydrogenated tallow derivative (about 72% octadecyl dimethylamine oxide, about 24% hexadecyl dimethylamine oxide, and about 3% tetradecyl dimethylamine oxide).

TABLE 11

Water Uptake (%) of Weathered SYP Treated Sticks

| Test solution | Day 0 | Day 220 | Day 610 |
|---|---|---|---|
| Untreated | 23 | 27 | 77 |
| 1% decyl dimethylamine oxide | 22 | 39 | 71 |
| 1% didecyldimethyl ammonium chloride | 17 | 22 | 36 |
| 1% hexadecyl dimethylamine oxide | 12 | 14 | 17 |

TABLE 12

Water Uptake (%) of Weathered SYP Treated Sticks

| Test solution | Day 0 | % WRE start (Day 0) | Day 90 | Day 310 | Day 480 |
|---|---|---|---|---|---|
| Untreated | 36 | — | 35 | 65 | 74 |
| 1% didecyldimethyl ammonium chloride | 17 | 53 | 24 | 36 | 29 |
| 1% hexadecyl dimethylamine oxide | 10 | 72 | 13 | 18 | 14 |
| 1% dodecyl dimethylamine oxide | 14 | 61 | 15 | 20 | 24 |
| 1% hexadecyl dimethylamine oxide and 0.5% didecyldimethyl ammonium chloride | 7 | 81 | 14 | 17 | 23 |

EXAMPLE 11

The procedure for determining waterproofing efficacy was repeated with southern yellow pine sticks, southern yellow pine end grain wafers, and ponderosa pine wafers and the aqueous solutions in Table 13 below by the procedure described in Example 10.

The results are shown in Table 13.

TABLE 13

| Test solution | Water Uptake % of Weathered Wood | | |
|---|---|---|---|
| | Day 0 | Day 100 | Day 225 |
| SYP sticks ¼ × ¾ × 10" | | | |
| Untreated | 37 | 45 | 55 |
| 1% didecyldimethyl ammonium chloride | 27 | 34 | 26 |
| 1.5% HT-AO and 0.75% dodecyl dimethylamine oxide | 9 | 11 | 8 |
| SYP end grain wafers | | | |
| Untreated | 40 | 71 | 77 |
| Thompson's Waterseal ™ [2] | 13 | | 24 |
| 1% didecyldimethyl ammonium chloride | 41 | 41 | 56 |
| 1.5% HT-AO[1] and 0.75% dodecyl dimethylamine oxide | 22 | 29 | 15 |
| Ponderosa Pine wafers | | | |
| Untreated | 75 | 89 | |
| Thompson's Waterseal ™ 2 | 11 | 12 | |
| 1% didecyldimethyl ammonium chloride | 62 | 73 | |
| 1.5% HT-AO[1] and 0.75% dodecyl dimethylamine oxide | 24 | 33 | |

[1]HT-AO is hydrogenated tallow derivative.
[2]Thompson's Waterseal is available from Thompson and Formby of Memphis, TN.

EXAMPLE 12

The efficacy of the aqueous amine oxide solutions in Table 14 at various concentrations against the wood rot fungi *T. versicolor* (white rot fungi), *G. trabeum* (brown rot fungi), *P. placenta* (brown rot fungi), and *C. globosum* (soft rot decay fungi) were determined using the agar dilution plate method well known in the art. The minimum concentration of each amine oxide required to achieve 100% growth retardation of each specific organism, i.e., the minimum inhibitory concentration (MIC), was determined. The percent retardation of the fungi was determined by the percentage change in the diameter of the fungi on the agar plate (i.e. Percent Retardation=((Diameter of Control)−(Diameter of Treated Fungi))/(Diameter of Control)*100%).

The results are shown in Table 14 below.

TABLE 14

| | MIC (ppm of amine oxides) | | | |
|---|---|---|---|---|
| Amine Oxide | T. versicolor (ppm) | G. trabeum (ppm) | P. placenta (ppm) | C. globosum (ppm) |
| Octyldimethylamine oxide | 750 | 1000 | 1000 | >1000 |
| Decyl-DMAO | 750 | 250 | 500 | >1000 |
| Coco-DMAO | 750 | 500 | 500–1000 | >1000 |
| Branched alkyl ($C_{10}$–$C_{14}$) DMAO | 500 | 250 | 500 | >1000 |
| Dodecyl-DMAO | 250 | 250 | 250 | >1000 |
| Tetradecyl-DMAO | >1000 | >1000 | >1000 | >1000 |
| Hexadecyl-DMAO | >1000 | >1000 | >1000 | >1000 |
| Oleyl-DMAO | >1000 | >1000 | >1000 | >1000 |
| Octadecyl-DMAO | >1000 | >1000 | >1000 | >1000 |
| Coco-di(hydroxyethyl)-amine oxide | 500 | 500 | 500 | >1000 |
| Tallow di(hydroxyethyl)-amine oxide | >1000 | >1000 | >1000 | >1000 |
| Dodecyl-BMAO | >1000 | 1000 | >1000 | >1000 |
| Lauryl morpholine N-oxide | 750 | 1000 | 500 | >1000 |

The minimum concentration of the aqueous amine oxide solutions in Table 15 required to achieve 50% growth retardation of each specific organism, i.e., $IC_{50}$, was estimated from the data obtained using Table2D curve fitting. The results are shown in Table 15.

TABLE 15

| | Barlox ® 12 | | Barlox ® 12i | | Bardac ® 2280 | |
|---|---|---|---|---|---|---|
| Fungi | $IC_{50}$ (ppm) | MIC (ppm) | $IC_{50}$ (ppm) | MIC (ppm) | $IC_{50}$ (ppm) | MIC (ppm) |
| T. versicolor | 51 | 750 | 84 | 500 | 28 | >1000 |
| G. trabeum | 9 | 250 | 44 | 250 | 8 | >1000 |
| P. placenta | 5 | 1000 | 89 | 500 | <5 | <1000 |
| C. globosum | 47 | >1000 | 153 | >1000 | 28 | >1000 |

Barlox ® 12 is an aqueous solution containing 30% by weight of coco-DMAO. Barlox ® 12i is an aqueous solution containing 30% by weight of branched ($C_{10}$–$C_{14}$) alkyl-DMAO. Bardac ® 2280 is 80% by weight of didecyl dimethyl ammonium chloride in ethanol and water

EXAMPLE 13

40" by ¾" by ¾" pieces of southern yellow pine lumber were treated with the aqueous solution prepared in Example 1 according to the procedure described in the American Wood Preservers' Association test method E7, which is hereby incorporated by reference. The procedure is generally as follows. The southern yellow pine lumber pieces were placed in a pressure treating cylinder for about 30 minutes at about −90 kPa, injected with the aqueous solution, and pressurized to about 800 kPa for about 30 minutes. The pressure was released by the addition of air and the solution was drained.

This procedure was repeated with aqueous solutions containing 0.5 or 1.0% by weight of copper chromium arsenate (CCA) and aqueous solutions containing 0.5, 1.0, or 1.5% by weight of didecyl dimethyl ammonium chloride (DDAC).

From each treated piece, two matched 18" stakes and one 4" center piece were obtained. The 18" stakes were placed in the ground at different field sites, field sites A and B. A total of 10 test stakes treated with each aqueous solution were placed in each field site. After 11 months, the stakes were observed. The results are shown in Table 16 below.

TABLE 16

| Aqueous Treatment Solution | Target Retention (kg/m³) | Field Site A Decay | Field Site A Termite Attack | Field Site B Decay | Field Site B Termite Attack |
|---|---|---|---|---|---|
| Untreated | — | 6.2 ± 2.4 | 4.4 ± 4.2 | 7.2 ± 4.2 | 8.5 ± 3.1 |
| 0.5% (w/w) CCA | 3 | 10 | 10 | 10 | 10 |
| 1.0% (w/w) CCA | 6 | 10 | 10 | 10 | 10 |
| 0.5% (w/w) DDAC | 3 | 9.9 ± 0.3 | 9.3 ± 0.9 | 10 | 10 |
| 1.0% (w/w) DDAC | 6 | 10 | 9.9 ± 0.3 | 10 | 10 |
| 1.5% (w/w) DDAC | 9 | 10 | 8.9 ± 1.3 | 10 | 10 |
| 0.82% (w/w) of coco-DMAO and 0.33% (w/w) of hexadecyl-DMAO at a 5:2 weight ratio | 5 (Coco) + 2 ($C_{16}$) | 9.5 ± 0. | 9.0 ± 1.2 | 9.9 ± 0.3 | 10 |
| 1.65% (w/w) of coco-DMAO and 0.67% (w/w) of hexadecyl-DMAO at a 5:2 weight ratio | 10 (coco) + 4 ($C_{16}$) | 10 | 9.8 ± 0.4 | 10 | 10 |
| 2.5% (w/w) of hexadecyl-DMAO and 1.0% (w/w) of coco-DMAO at a 5:2 weight ratio | 15 (coco) + 6 ($C_{16}$) | 9.8 ± 0.4 | 9.9 ± 0.3 | 10 | 10 |

The target retention is the desired amount of the ingredient to be retained in the wood substrate.
*A rating of 10 means that all 10 stakes remained in tact and free of decay or termite attack. A rating of 0 means that the stakes were completely decayed or attacked by termites.

EXAMPLE 14

The wood preserving efficacy of each aqueous test solution in Table 17 below was tested on freshly cut tulip wood (also known as Tulip-Popular, Yellow Popular, and *Liriodendron tulipfera* L.) as follows. All percentages in Table 17 are by weight. Pieces of tulip wood cut from a 4" debarked branch were cut into pieces. Each piece was then split into 4 sections. Each section was dipped into the test solution for about 1 minute and blotted with a paper towel to remove excess liquid. The sections were sealed in a clear plastic bag and stored at ambient conditions. The sections were observed after 1, 3, 7, and 11 weeks for the growth of stains, molds, and fungi. The aqueous test solutions were prepared by mixing the active ingredient with water. The results are shown in Table 17.

TABLE 17

| Aqueous test solution | Rating* of treated tulip sections vs. Time | | | |
|---|---|---|---|---|
| | 1 week | 3 weeks | 7 weeks | 11 weeks |
| None | 3 | 2.5 | 2 | 1 |
| Water | 4 | 2 | 1 | 1 |
| 0.65% Didecyldimethyl ammonium chloride | 4 | 4 | 4 | 4 |
| 0.32% Didecyldimethyl ammonium chloride | 4 | 4 | 3.5 | 3.5 |
| 1.0% Hexadecyl DMAO and 0.4% Dodecyl DMAO | 4 | 3 | 2 | 1 |
| 0.5% Hexadecyl DMAO and 0.2% Dodecyl DMAO | 5 | 5 | 3 | 2 |
| 1.0% Hexadecyl DMAO, 0.4% Dodecyl DMAO, and 0.15% 1-Hydroxyethylidene-1,1-diphosphonic acid (HEDP) | 4 | 4 | 3.5 | 3 |
| 0.5% Hexadecyl DMAO, 0.2% Dodecyl DMAO, and 0.08% HEDP | 4 | 4 | 2 | 1 |
| 1.0% Hexadecyl DMAO, 0.4% Dodecyl DMAO, and 0.045% Ammonia | 4 | 4 | 3.5 | 3 |
| 1.0% Hexadecyl DMAO, 0.4% Dodecyl DMAO, 0.15% HEDP, and 0.045% Ammonia | 4 | 4 | 3 | 2 |
| 1.0% Dodecyl DMAO | 4 | 4 | 4 | 4 |
| 0.5% Dodecyl DMAO | 4 | 3 | 2 | 1 |
| 1.0% Dodecyl DMAO and 0.045% Ammonia | 3 | 3 | 2 | 1 |
| 1.0% Dodecyl DMAO and 0.15% HEDP, and 0.045% Ammonia | 3.5 | 3.5 | 3 | 2 |
| None | 3 | 3 | 2 | — |
| 1.0% Dodecyl DMAO | 4 | 4 | 3 | — |
| 1.0% Dodecyl DMAO and 1.0% Coco-dimethyl amine[1] | 4 | 4 | 3.5 | — |
| 1.0% Dodecyl DMAO and 0.5% Coco-dimethyl amine | 4 | 4 | 4 | — |
| 1.0% Dodecyl DMAO and 0.25% Coco-dimethyl amine | 4 | 4 | 4 | — |
| 0.5% Hexadecyl dimethylamine oxide and 0.5% dodecyldimethyl amine oxide | 4 | 3 | 3 | 3 |

*Rating scale:
4 - Clean with no visible stain or mold
3 - Trace amount of white/black fungal growth
2 - Black and/or white fungal growth visible on all faces and ends
1 - Heavy fungal growth
[1] Coco-dimethylamine is available as Barlene ® 12C from Lonza Inc. of Fair Lawn, NJ.

EXAMPLE 15

The wood preserving efficacy of each aqueous test solution in Table 18 below was tested on freshly cut beech wood (*Fagus grandifolia Ehrh.*) as follows. All percentages in Table 18 are by weight. A 1" branch of a beech tree was split into two pieces. The bark was left on the pieces. Each piece was dipped into the test solution for about 1 minute and blotted with a paper towel to remove excess liquid. The pieces were sealed in a clear plastic bag and stored at ambient conditions. The pieces were observed after 1, 3, 7, and 11 weeks for the growth of stains, molds, and fungi. The aqueous test solutions were prepared by mixing the active ingredient with water. The results are shown in Table 18.

TABLE 18

| Aqueous test solution | Rating* of treated tulip sections vs. Time | | | |
|---|---|---|---|---|
| | 1 week | 3 weeks | 7 weeks | 11 weeks |
| None | 3 | 3 | 2 | 1 |
| Water | 4 | 3 | 2 | 1 |
| 0.65% Didecyldimethyl ammonium chloride | 4 | 3.5 | 2 | 2 |
| 0.32% Didecyldimethyl ammonium chloride | 4 | 2 | 2 | 2 |
| 1.0% Hexadecyl DMAO and 0.4% Dodecyl DMAO | 4 | 2 | 1 | 1 |
| 0.5% Hexadecyl DMAO and 0.2% Dodecyl DMAO | 4 | 3 | 2 | 1 |
| 1.0% Hexadecyl DMAO, 0.4% Dodecyl DMAO, and 0.15% 1-Hydroxyethylidene-1,1-diphosphonic acid (HEDP) | 4 | 3.5 | 2.5 | 2 |
| 0.5% Hexadecyl DMAO, 0.2% Dodecyl DMAO, and 0.08% HEDP | 4 | 3 | 2 | 1 |
| 1.0% Hexadecyl DMAO, 0.4% Dodecyl DMAO, and 0.045% Ammonia | 4 | 2 | 2 | 1 |
| 1.0% Hexadecyl DMAO, 0.4% Dodecyl DMAO, 0.15% HEDP, and 0.045% Ammonia | 4 | 3 | 2.5 | 2 |
| 1.0% Dodecyl DMAO | 4 | 2 | 2 | 2 |
| 0.5% Dodecyl DMAO | 4 | 4 | 2.5 | 2.5 |
| 1.0% Dodecyl DMAO and 0.045% Ammonia | 4 | 3 | 2.5 | 2 |
| 1.0% Dodecyl DMAO and 0.15% HEDP, and 0.045% Ammonia | 4 | 2.5 | 2 | 2 |
| None | 3.5 | 3 | 2.5 | — |
| 1.0% Dodecyl DMAO | 3.5 | 3 | 2 | 1 |
| 1.0% Dodecyl DMAO and 1.0% Coco-dimethyl amine[1] | 4 | 3.5 | 3.5 | — |
| 1.0% Dodecyl DMAO and 0.5% Coco-dimethyl amine | 3.5 | 2 | 2 | 1 |
| 1.0% Dodecyl DMAO and 0.25% Coco-dimethyl amine | 4 | 3 | 2 | — |

*Rating scale:
4 - Clean with no visible stain or mold
3 - Trace amount of white/black fungal growth
2 - Black and/or white fungal growth visible on all faces and ends
1 - Heavy fungal growth
[1] Coco-dimethylamine is available as Barlene ® 12C from Lonza Inc. of Fair Lawn, NJ.

All patents, applications, articles, publications, and test methods mentioned above are hereby incorporated by reference.

Many variations of the present invention will suggest themselves to those skilled in the art in light of the above detailed description. Such obvious variations are within the full intended scope of the appended claims.

What is claimed is:

1. A wood preservative composition consisting essentially of a solvent and from about 0.1 to about 5% by weight of one or more amine oxides as the sole active ingredient based upon 100% total weight of the wood preservative composition, the wood preservative composition being substantially free of chlorophenols and quaternary ammonium compounds, wherein the amine oxides are solely responsible for inhibiting the microbial growth in wood and the amine oxides are selected from the group consisting of:
   (I) a trialkylamine oxide having the general formula $R^1R^2R^3N$——$O$, wherein $R^1$ is a linear or cyclic $C_8$ to $C_{40}$ saturated or unsaturated group; and $R^2$ and $R^3$ independently are linear $C_1$ to $C_{40}$ saturated or unsaturated groups;
   (ii) an alkylcyclicamine oxide;
   (iii) a dialkylpiperazine di-N-oxide;
   (iv) an alkyldi(poly(oxyalkylene))amine oxide;
   (v) a dialkylbenzylamine oxide;
   (vi) a fatty acylamidopropyldimethylamine oxide
   (vii) a diamine oxide;
   (viii) a triamine oxide; and
   (ix) any combination of any of the foregoing;
   said wood preservative composition optionally further consisting essentially of a component selected from the group consisting of corrosion inhibitors, iron stain inhibitors and mixtures thereof.

2. The wood preservative composition of claim 1, wherein the composition consists essentially of a sapstain inhibiting effective amount of one or more amine oxides.

3. The wood preservative composition of claim 1, wherein $R^1$ is a linear or cyclic $C_8$ to $C_{22}$ saturated or unsaturated group; and $R^2$ and $R^3$ independently are linear $C_1$ to $C_{22}$ saturated or unsaturated groups.

4. The wood preservative composition of claim 1, wherein the wood preservative composition is free of chlorine containing compounds and quaternary ammonium compounds.

5. The wood preservative composition of claim 1, wherein the wood preservative composition is free of chlorophenols and quaternary ammonium compounds.

6. The wood preservative composition of claim 1, wherein said solvent is water.

7. The wood preservative composition as defined in claim 1, wherein said trialkylamine oxide is a dialkylmethylamine oxide having the formula $R^1R^2CH_3N{\rightarrow}O$, wherein $R^1$ is a linear cyclic $C_8$ to $C_{40}$ saturated or unsaturated group; and $R^2$ is a linear $C_1$ to $C_{40}$ saturated or unsaturated group.

8. The wood preservative composition as defined in claim 7, wherein $R^1$ is a linear or cyclic $C_8$ to $C_{22}$ saturated or unsaturated group; and $R^2$ is a linear $C_1$ to $C_{22}$ saturated or unsaturated group.

9. The wood preservative of claim 1, wherein the wood preservative composition consists essentially of from about 0.5 to about 2% by weight of amine oxide, based upon 100% total weight of the wood preservative composition.

10. The wood preservative of claim 9, wherein the wood preservative composition consists essentially of from about 1 to about 2% by weight of amine oxide, based upon 100% total weight of the wood preservative composition.

11. The wood preservative composition of claim 1, wherein said trialkylamine oxide is an alkyldimethylamine oxide having the formula $R^1(CH_3)_2N{\rightarrow}O$, wherein $R^1$ is a linear or cyclic $C_8$ to $C_{40}$ saturated or unsaturated group.

12. The wood preservative composition of claim 11, wherein said alkyldimethylamine oxide is selected from the group consisting of a $C_{10}$ alkyldimethylamine oxide, $C_{10}$–$C_{14}$ alkyldimethylamine oxide, $C_{16}$–$C_{18}$ alkyldimethylamine oxide, and any combination of any of the foregoing.

13. The wood preservative composition of claim 11, wherein $R^1$ is a linear or cyclic $C_8$ to $C_{22}$ saturated or unsaturated group.

14. The wood preservative composition of claim 13, wherein $R^1$ is a linear $C_{10}$ to $C_{18}$ alkyl.

15. The wood preservative composition of claim 14, wherein $R^1$ is a linear $C_{10}$ to $C_{16}$ alkyl.

16. The wood preservative composition of claim 1, wherein the composition consists essentially of a fungicidally effective amount of one or more amine oxides.

17. The wood preservative composition of claim 16, wherein the wood preservative composition consists essentially of a mixture of two or more different species of amine oxide.

18. The wood preservative composition of claim 16, wherein the wood preservative composition consists essentially of a waterproofing and fungicidally effective amount of amine oxide.

19. The wood preservative composition of claim 16, further consisting essentially of a component selected from the group consisting of corrosion inhibitor, iron stain inhibitor, and mixtures thereof.

20. The wood preservative composition of claim 19, wherein the iron stain inhibitor is a phosphonic iron stain inhibitor.

* * * * *